(12) United States Patent
Kanare et al.

(10) Patent No.: US 8,047,056 B2
(45) Date of Patent: Nov. 1, 2011

(54) MOISTURE VAPOR PROBE

(75) Inventors: Howard M. Kanare, Wilmette, IL (US);
Ed Wagner, Rogue River, OR (US);
Tim Duncan, Grant's Pass, OR (US)

(73) Assignee: Construction Technology Laboratories, Inc., Skokie, IL (US)

( * ) Notice: Subject to any disclaimer, the term of this patent is extended or adjusted under 35 U.S.C. 154(b) by 463 days.

(21) Appl. No.: 12/254,472

(22) Filed: Oct. 20, 2008

(65) Prior Publication Data

US 2009/0100926 A1    Apr. 23, 2009

Related U.S. Application Data

(60) Provisional application No. 60/981,796, filed on Oct. 22, 2007.

(51) Int. Cl.
*G01N 7/14* (2006.01)

(52) U.S. Cl. .................. 73/29.01; 73/73; 73/335.02

(58) Field of Classification Search ............. 73/335.02
See application file for complete search history.

(56) References Cited

U.S. PATENT DOCUMENTS

| | | | |
|---|---|---|---|
| 2,017,376 A | 10/1935 | Rother et al. |
| 3,581,197 A | 5/1971 | Morey |
| 3,680,364 A | 8/1972 | Carrier |
| 3,788,128 A | 1/1974 | Strohecker |
| 3,870,951 A | 3/1975 | Brown et al. |
| 3,927,370 A | 12/1975 | De Bough |
| 3,968,428 A | 7/1976 | Numoto |
| 4,020,417 A | 4/1977 | Brehob et al. |
| 4,069,716 A | 1/1978 | Vanasco et al. |
| 4,268,824 A | 5/1981 | Phillips |
| 4,399,404 A | 8/1983 | Resh |
| 4,445,788 A | 5/1984 | Twersky et al. |
| 4,514,722 A | 4/1985 | Batcheler et al. |
| 4,543,820 A | 10/1985 | Handy et al. |
| 4,567,563 A | 1/1986 | Hirsch |
| 4,711,244 A | 12/1987 | Kuzara |
| 4,868,491 A | 9/1989 | Black |

(Continued)

FOREIGN PATENT DOCUMENTS

DE    1037136 A1    8/1958

(Continued)

OTHER PUBLICATIONS

"Concrete, Hardened: Relative Community Measured in Drilled Holes," Nordtest Method; NT Build 739; ISSN 039-7253, 1995.

(Continued)

*Primary Examiner* — Hezron E Williams
*Assistant Examiner* — Paul West
(74) *Attorney, Agent, or Firm* — Foley & Lardner LLP

(57) ABSTRACT

One embodiment of the invention comprises a moisture vapor probe comprising a hollow sleeve and a removable electronics module. The probe has a generally cylindrical hollow sleeve having a sidewall with an inner surface and an outer surface. The sleeve comprises a sensor plate having a moisture vapor sensor and forming a water impermeable barrier with the sidewall. The sleeve has an opening such that a volume is defined by the opening, the sidewall and the sensor plate. The probe further comprises an electronics module removably disposable within the sleeve. The electronics module includes an information transfer unit. The information transfer unit in communication with the moisture vapor sensor and adapted to receive relative humidity information from the moisture vapor sensor.

17 Claims, 3 Drawing Sheets

U.S. PATENT DOCUMENTS

| | | | |
|---|---|---|---|
| 4,929,885 A | 5/1990 | Dishman |
| 5,023,560 A | 6/1991 | Gallagher |
| 5,382,908 A | 1/1995 | Forsstrom et al. |
| 5,488,312 A | 1/1996 | Havener et al. |
| 5,621,391 A | 4/1997 | Elseth |
| 5,730,024 A | 3/1998 | Sahlen |
| 6,076,396 A | 6/2000 | Dadachanji et al. |
| 6,422,061 B1 | 7/2002 | Sunshine et al. |
| 6,553,813 B2 | 4/2003 | Rynhart et al. |
| 6,601,440 B1 | 8/2003 | Chuang |
| 6,700,395 B1 | 3/2004 | Perry |
| 6,793,146 B2 | 9/2004 | Cunkelman et al. |
| 6,975,236 B2 | 12/2005 | Staples |
| 7,231,815 B2 | 6/2007 | Kanare |
| 2004/0140902 A1 | 7/2004 | Staples |
| 2006/0272392 A1* | 12/2006 | Kanare | 73/29.02 |

FOREIGN PATENT DOCUMENTS

| | | |
|---|---|---|
| DE | 4427244 A1 | 2/1996 |
| GB | 653193 A | 5/1951 |
| GB | 2353360 A | 2/2001 |
| JP | 01242948 A | 9/1989 |
| JP | 11 304764 A | 11/1999 |
| JP | 2004 279394 A | 10/2004 |
| WO | WO 97/45726 | 12/1997 |
| WO | WO 2004/102187 A | 11/2004 |
| WO | WO 2006/060016 | 6/2006 |

OTHER PUBLICATIONS

"Standard Test Method for Determining Relative Humidity in Concrete Floor Slabs Using in situ Probes", ASTM International; Designation: F 2170-02, 2007.

* cited by examiner

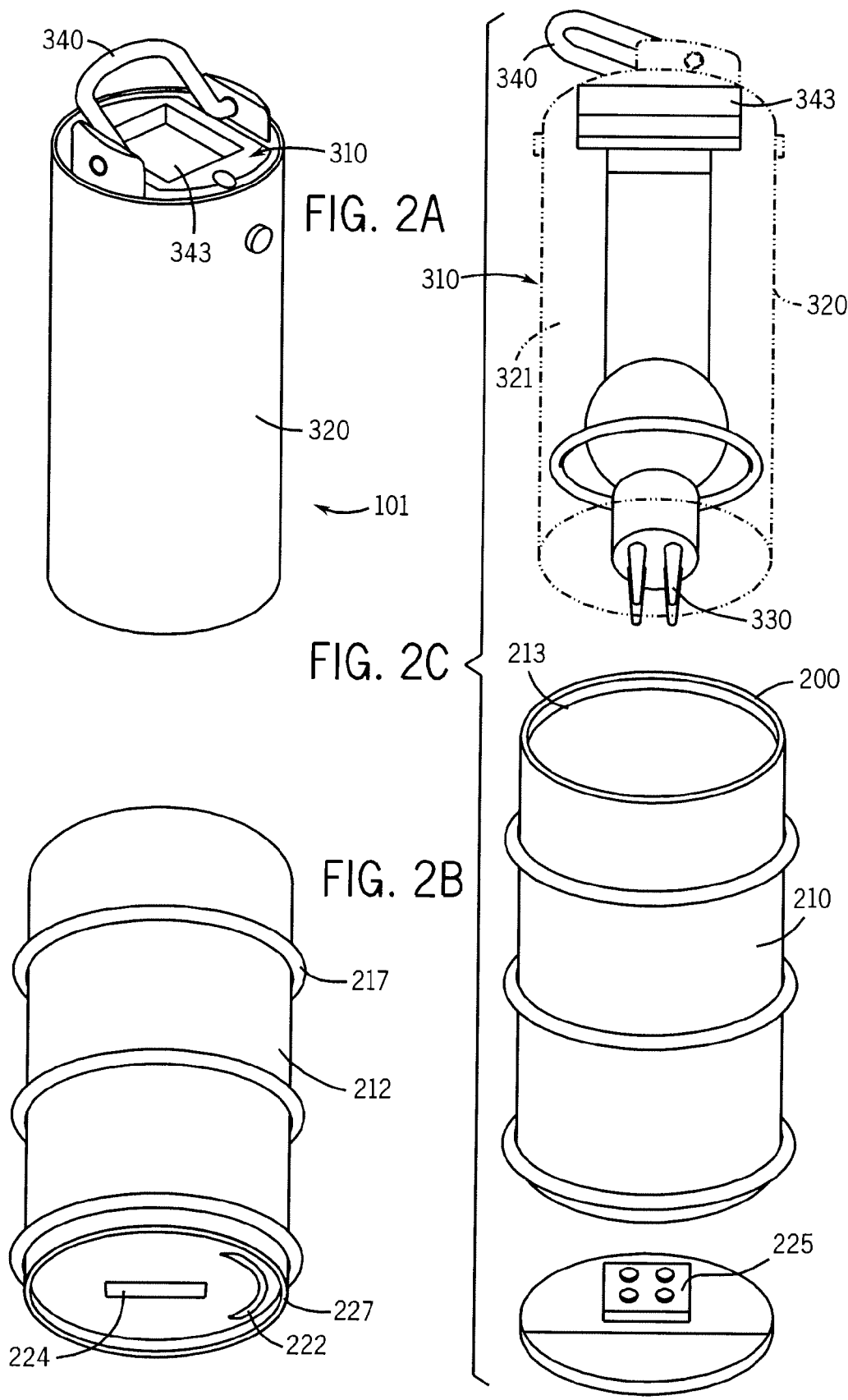

US 8,047,056 B2

MOISTURE VAPOR PROBE

CROSS-REFERENCE TO RELATED PATENT APPLICATION

This application claims priority from U.S. Provisional Patent Application 60/981,796 filed Oct. 22, 2007, herein incorporated by reference in its entirety.

FIELD OF THE INVENTION

One embodiment of the invention relates to a relative humidity (RH) probe having a sleeve with a moisture vapor sensor and an electronics module removable there from.

BACKGROUND OF THE INVENTION

Commercially available moisture probes typically are one-use devices that result in significant waste and expense or are reusable but must be re-calibrated or checked for accuracy before new use. Re-calibrating a reusable probe before use requires significant time. In addition, reusable probes may become inaccurate due to aging, but typically users do not have the equipment and capability to check the accuracy of their probes. Therefore, reusable probes are often used for many months or even years without being tested for accuracy. Use of inaccurate probes can lead the user to make inappropriate decisions and significant problems based on incorrect data: for example, if a moisture probe indicates that a concrete floor is dry enough to receive a floor covering or coating, but the floor is in reality too wet, then a floor covering or coating will be installed which later will fail due to the unrecognized high moisture condition. Use of inaccurate probes can, thus, have a significant economic impact on a commercial facility when floor coverings or coatings must be repaired or replaced after the facility has been put into operation.

In addition, commercially available relative humidity probes are expensive because they comprise a sensing element and electronics package all in the probe head that is inserted into the concrete. In addition, cost is a very relevant factor in the adoption of moisture probe technology. Typical prices of moisture probes commercially available in the United States range from $50 to over $250, and the cost of associated handheld meters ranges from several hundred dollars to nearly $700. Compared to anhydrous calcium chloride test kits (ASTM F1869) which cost approximately $8.00 per test, the high price of moisture probes has been a barrier to wide-spread acceptance in the floor coverings and coatings industry for preinstallation testing.

Further, commercially available probe systems often employ an outer housing and an inner housing, the outer housing used to line the drilled hole in concrete to isolate the sidewall of the hole from the sensor which is positioned inside the inner housing. Prior art systems utilize fins along the sidewall of the outer housing to define a volume. This volume represents a "dead volume" that serves as the volume the sensor tests. In prior art systems the volume is defined by a portion of the sidewall of the hole, the space between the outer housing and the inner housing and the space between the inner housing and the sensor plus any additional volume within the sensor housing. Thus, because the probe itself takes up a significant volume within the sleeve, a typical commercially available probe has a large volume (for example some systems have a volume around 2650 $mm^3$) which must equilibrate with the concrete.

Probes using existing technology require longer than desirable times to equilibrate, an issue which is magnified for reusable probes that require calibration checking before use. For example, users currently place probes in concrete and have to return to the jobsite three days later to obtain readings, in accordance with ASTM F2170-02, "Standard Test Method for Determining Relative Humidity in Concrete Floor Slabs Using in situ Probes."

SUMMARY OF THE INVENTION

One embodiment of the invention relates to a moisture vapor probe. The moisture vapor probe comprises a generally cylindrical hollow sleeve having a sidewall with an inner surface and an outer surface, the sleeve further having a first end and a second end; the first end having a sensor plate disposed proximate thereto and forming a water impermeable barrier with the sidewall, the second end of the sleeve having an opening such that a volume is defined by the opening, the sidewall and the sensor plate. The sensor plate having an inner surface and an outer surface, a moisture vapor sensor disposed on the outer surface of the sensor plate in electrical communication with a communication port on the inner surface of the sensor plate. The moisture vapor probe further comprises an electronics module disposable substantially within the sleeve, the electronics module having a housing shaped to substantially fit within the sleeve, the housing having a first end corresponding to the first end of the sleeve and a second end corresponding to the second end of the sleeve and having a communication port positioned substantially at the first end of the housing. The electronics module communication port is engagable with the sleeve communication port. The housing of the electronic module further comprises a handle at a second end, the handle engagable by a user when the housing is disposed in the sleeve. The electronics module further comprises an information transfer unit, the information transfer unit in communication with relative humidity information from the moisture vapor sensor via the sensor plate communication port and the housing communication port.

Another embodiment of the invention relates to a method of measuring the relative humidity of a surface. The method comprises the steps of drilling a plurality of holes in a surface, each hole having a sidewall, a bottom and an opening; placing in each hole a generally cylindrical hollow sleeve having a sidewall with an inner surface and an outer surface, the sleeve further having a first end and a second end, the first end having a sensor plate disposed proximate thereto and forming a water impermeable barrier with the sidewall, the sensor plate having a fin extending away from the sensor plate and positioned circumferentially about the sensor plate and the sensor plate further comprising a moisture vapor sensor; defining a dead volume for testing the relative humidity of the surface, the dead volume defined by the bottom of the hole, the sensor plate, and the sensor plate fin; inserting into one of the sleeves an electronics module; determining a moisture vapor content value of air in the dead volume; transmitting the determined moisture vapor content value to the electronics module. For each hole, the electronics module is inserted and the moisture vapor content value for that hole is determined.

In yet another embodiment, the invention comprises a two-part moisture vapor probe. The probe has a generally cylindrical hollow sleeve having a sidewall with an inner surface and an outer surface. The sleeve comprises a first end and a second end; the first end having a sensor plate disposed proximate thereto and forming a water impermeable barrier with the sidewall. The second end of the sleeve has an opening such that a volume is defined by the opening, the sidewall and the sensor plate, the sensor plate having a moisture vapor sensor. The probe further comprises an electronics module removably disposable within the sleeve. The electronics module includes an information transfer unit. The information transfer unit in communication with the moisture vapor sensor and adapted to receive relative humidity information from the moisture vapor sensor.

These and other objects, advantages, and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 2A is a perspective view of one embodiment of the electronics module;

FIG. 2B is a perspective view of one embodiment of the sleeve;

FIG. 2C is an exploded perspective view of one embodiment of the moisture vapor probe.

DETAILED DESCRIPTION OF PREFERRED EMBODIMENTS

Figure 1A:
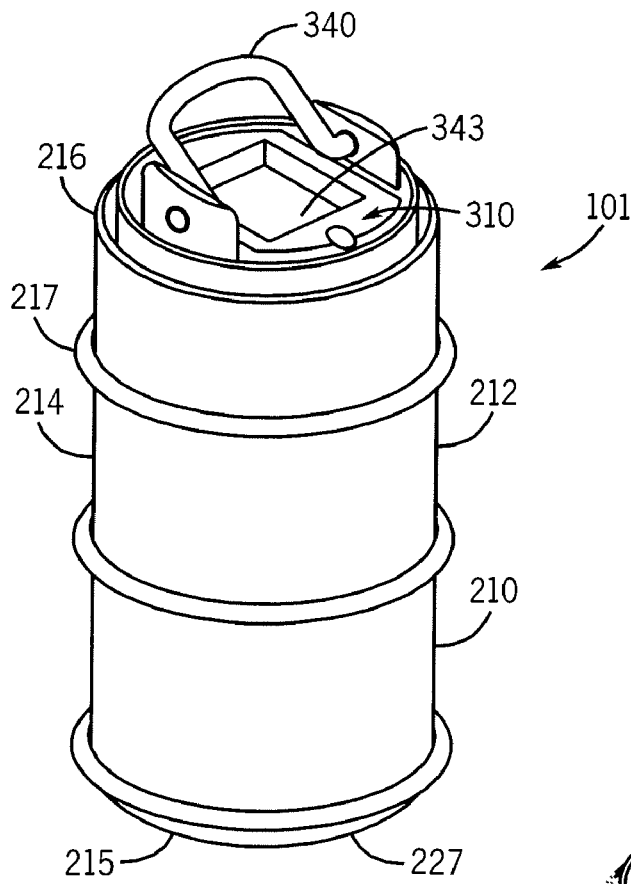
FIG. 1A is a perspective view of one embodiment of the moisture vapor probe.

Referring to FIGS. 1A 1B, and 2A-C, one embodiment of the invention relates to a moisture vapor probe 101 with an integrated sleeve 210 with a removable electronics module 310 capable of being inserted into the sleeve 210. The sleeve 210 (best shown in FIGS. 1A, 1B, 2B, and 2C) is a generally cylindrical hollow sleeve 210 having a sidewall 212 with an inner surface 213 and an outer surface 214, the sleeve 210 further having a first end 215 and a second end 216. The outer surface 214 of the sidewall 212 includes, in one embodiment, one or more fins 217 positioned circumferentially about the sleeve 210. The sleeve first end 215 having a sensor plate 220 disposed proximate to the sleeve second end 216. The sleeve side wall inner surface 213 and the sensor plate 220 form a water impermeable barrier, preventing moisture vapor from entering the sleeve 210 from the sleeve first end 215. Thus, the sidewall 212 is sealed into the sleeve 210 facing downward (in relation to a hole for testing relative humidity) so that moisture vapor cannot diffuse past the sensor plate 220. The second end 216 of the sleeve 210 includes an opening 230. Thus a volume 232 is defined by the opening 230, the sidewall 212 and the sensor plate 220.

The sensor plate 220 (best shown in FIGS. 1B and 2C) of the sleeve 210 includes an inner surface 221 and an outer surface 222. The sensor plate inner surface 221 is interior to the sleeve 210, i.e. facing into the volume 232. The sensor plate outer surface 222 is exterior to the volume 232, i.e. faces away from the volume 232. A moisture vapor sensor 224 is disposed on the outer surface 222 of the sensor plate 220. Thus the moisture vapor sensor 224 is exposed to the environment external to the sleeve 210. The sensor plate 220 and sleeve 210 thus form a "piston" that displaces air from the test hole, and further forming a small test volume at the bottom of the hole, and creating a seal to define a test volume 337 within which the moisture vapor sensor 224 resides. The seal between the sensor plate 220 and the sidewall 212 serves to isolate the moisture vapor sensor in a testing volume 337 (of air).

Figure 1B:
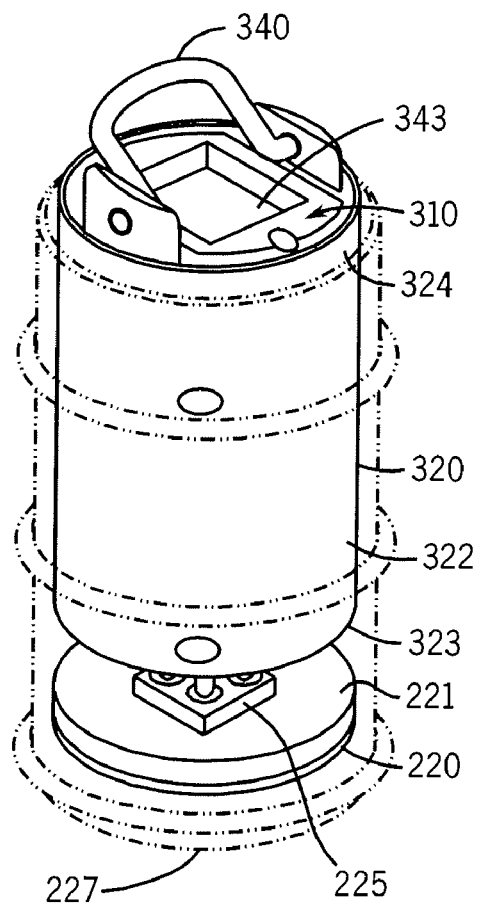
FIG. 1B is a partial cut-away perspective view of the moisture vapor probe of FIG. 1A.

In one embodiment shown in FIG. 1B, the sensor plate 220 further includes a sensor plate communication port 225 on the inner surface 221 of the sensor plate 220. The sensor plate communication port 225 is in communication with the moisture vapor sensor 224 such that the sensor plate communication port 225 receives relative humidity information from the moisture vapor sensor 224. In one embodiment, the relative humidity information is digital information.

The electronics module 310 (best shown in FIGS. 1B, 2A, and 2C) is adapted to be disposable substantially within the sleeve 210. The electronics module 310 includes a housing 320. The housing 320 is substantially cylindrical and has a diameter equal to (where the housing 320 is at least partially deformable) or less than the diameter of sleeve 210. The housing 320 includes a housing inner surface 321 and a housing outer surface 322, the outer surface 322 adjacent (i.e. facing) the sleeve inner surface 213. The housing 320 having a first end 323 corresponding to the first end 215 of the sleeve 210 and a second end 324 corresponding to the second end 216 of the sleeve 210.

The electronics module 310 further including an electronic module communication port 330. The electronic module communication port 330 is engagable with the sensor plate communication port 225. The electronic module communication port 330 is, in one embodiment, positioned substantially at the first end 323 of the housing 320.

Figure 3:
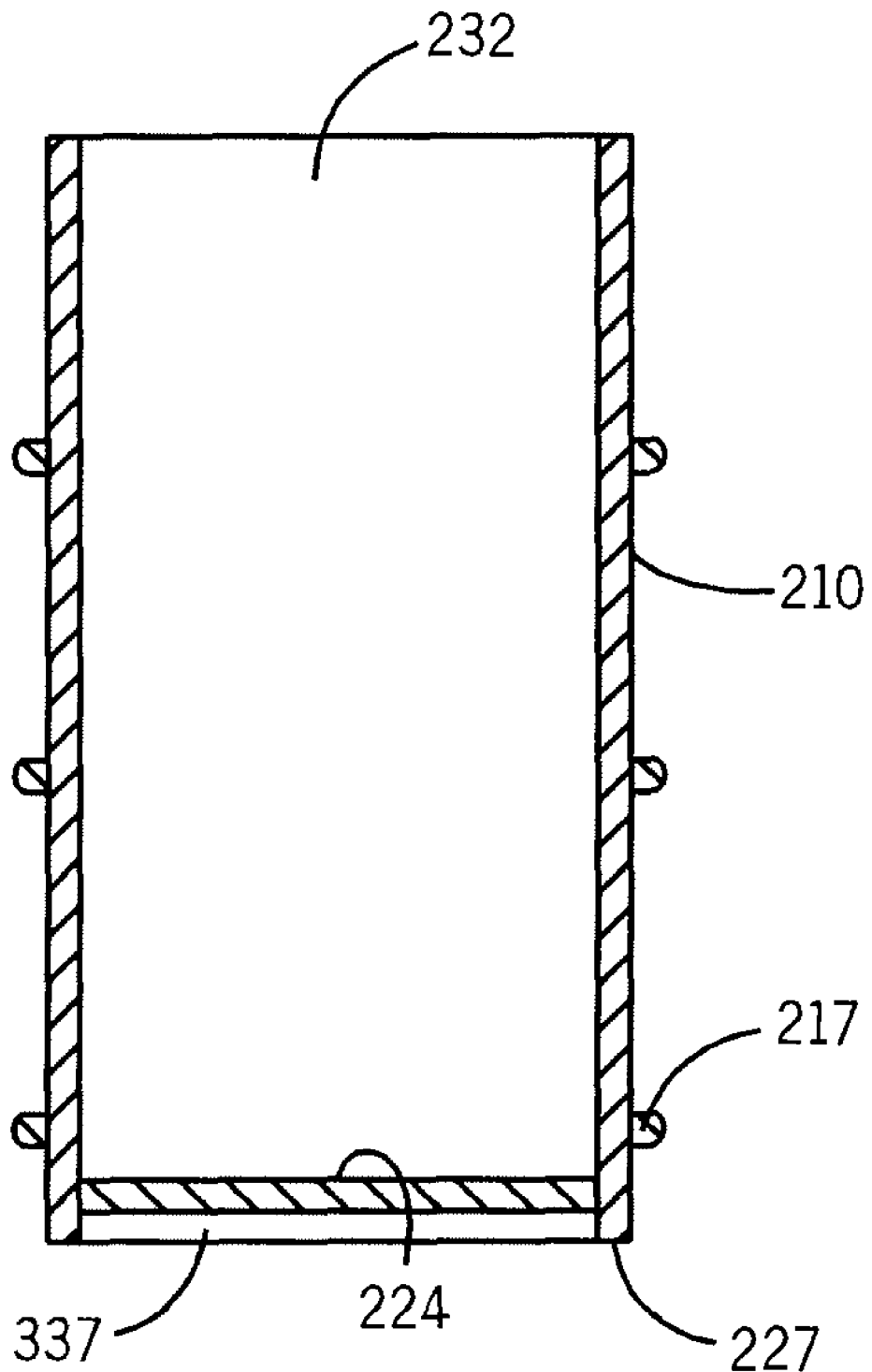
FIG. 3 is an illustration of the sleeve positioned in a hole.

In one embodiment, the housing 320 is substantially disposed within the sleeve 210, with both the sleeve 210 and housing 320 substantially disposed within a hole in floor, such as concrete. In one embodiment, the sleeve 210 is not easily removably from the hole, such as by interaction of the sleeve sidewall fins 217 with the sidewall of the hole (FIG. 3).

In one embodiment, the housing 320 of the electronic module 310 further comprises a handle 340 at the second end 324 of the electronics module 310. The handle 340 engagable by a user when the housing 320 is disposed in the sleeve 210, such that the user is able to utilize the handle 340 to remove the electronic module 310 from the sleeve 210.

In one embodiment, the electronics module 310 further comprises an information transfer unit 343, the information transfer unit 343 in communication with relative humidity information from the moisture vapor sensor 224 via the sensor plate communication port 225 and the housing communication port 330.

In one embodiment, the outer surface 222 of the sensor plate 220 includes a sensor plate fin 227 extending substantially perpendicular from the sensor plate outer surface 222 (i.e., generally parallel to a long axis of the sleeve 210). As seen in FIG. 3, the sensor plate fin 227 forms a seal between the outer surface 222 of the sensor plate 220 and the material being tested, thus creating a "testing" volume 337, which in this embodiment has a small cylindrical volume. The use of the sensor plate fin 227 allows for the definition of a precise volume (the testing volume 337) at the bottom of a sample hole permitting measurement at a precise depth in the concrete and allowing for ease of replication of that depth in additional sample holes. This is important in order to measure the moisture at a precise depth for certain applications. In addition, the testing volume 337 is minimized though the use of the above described structures. This provides a relatively small, in comparison to existing devices, testing volume. The larger the testing volume, the longer equilibration time will be needed. Thus, the use of a small volume permits more rapid equilibration than with current moisture vapor probes.

In one embodiment, the sleeve 210 is essentially designed to be "disposable" in the sense that is (or can be) left in the surface being tested. The moisture vapor sensor is designed to be placed into a drilled hole (as described further infra) and then the electronics module 310 is inserted into the sleeve 210 to determined moisture related characteristics, such as, but not limited to, percent relative humidity, temperature, dew point and related moisture conditions. The electronics module 310 can either be left in the sleeve 210 for repeated readings or removed and reused to read sensors at other locations. However, since the electronics module 310 generally contains the electronics (except for the sensor chip itself) and the sleeve 210 only holds a (in one embodiment, mechanically fastened) moisture vapor sensor chip, the disposable portion of the device can be low cost; and the more complex and expensive electronics module 310 is reusable. For embodiments where the electronics module 310 fits completely within the sleeve 210, the combined sensor assembly can remain in a concrete floor, for example, and not be subject to damage from activities or traffic. Thus, that embodiment is especially suitable to be installed to monitor the moisture in a structure even for long periods of time and to be protected against physical damage (to the moisture vapor probe).

The sleeve 210 is designed not to be re-used. It cannot be removed from the concrete without damage to the sealing fins and therefore cannot be reliably re-used. Because it is designed to be used in a single hole, this eliminates the possible re-use of un-calibrated and inaccurate probes.

In one embodiment, the testing volume is approximately 508 mm$^3$, while conventional probes have a volume of 2650 mm$^3$.

The electronics module 310 that is inserted into the sleeve 210 can have a multitude of features. For example, the information transfer unit 343 may comprise one or more of a graphical display (shown in FIG. 1A as an LCD), a wireless communication device, a wired communication device, a memory unit, or an audio unit. For example, one embodiment comprises a digital display for human readable results of RH measurements. Another embodiment utilizes a memory unit for providing data logging capability. Yet another embodiment includes the capability to accept a removable memory card such as, but not limited to, a Micro SD Memory Card for manual transfer of electronic data (including data-logging type information) to an external device such as a personal computer. In yet another embodiment, wireless capability is provided so that a user can interrogate the reader with a local handheld unit and download data wirelessly. In yet another embodiment, wireless transmission capability is provided as a part of a wireless mesh network, for example, but not limited to, using technology such as IEEE 802.15.4 (known as "Zigbee"). It should be appreciated that combinations of these and other user data transfer technologies could be implemented into the electronics module 310.

In one example, holes were drilled and probes placed in high moisture concrete having roughly 99% relative humidity. Commercially available probes achieved 95% of their final reading within 30-60 minutes after placement in drilled holes. By comparison, one embodiment of the present invention achieved 93% of its final reading within ten minutes after placement in drilled holes. Increased rapidity of equilibration provides a multitude of potential benefits depending on the application of the moisture vapor probe. For example, one potential benefit in the flooring area is that a quick equilibration will allow a user to test flooring and determine on the same day if flooring can be applied, preventing multiple trips and wasted "down time".

In a second example, probes were placed in low moisture concrete at approximately 60% RH, which is below the currently defined maximum limit for installation of resilient floor coverings in ASTM F710-05 "Standard Practice for Preparing Concrete Floors to Receive Resilient Flooring" is 75% RH. Two brands of commercially available probes were tested. They took from one hour to five hours to indicate a slab had less than 75% RH. In contrast, one embodiment of the described moisture vapor probe indicated less than 75% RH in about 10 minutes. This represents a 600% to a 3000% improvement and is immensely faster than the three days currently required in ASTM F2170-02, "Standard Test Method for Determining Relative Humidity in Concrete Floor Slabs Using in situ Probes." This rapid equilibration means that a user can obtain much more rapid results than with existing technology and make practical decisions faster, thereby saving time and money.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A moisture vapor probe comprising:
    a generally cylindrical hollow sleeve having a sidewall with an inner surface and an outer surface, the sleeve further having a first end and a second end;
    the first end having a sensor plate disposed proximate thereto and forming a water impermeable barrier with the sidewall, the second end of the sleeve having an opening such that a volume is defined by the opening, the sidewall and the sensor plate;
        the sensor plate having an inner surface and an outer surface, a moisture vapor sensor disposed on the outer surface of the sensor plate in electrical communication with a communication port on the inner surface of the sensor plate;
        an electronics module disposable substantially within the sleeve, the electronics module having a housing shaped to substantially fit within the sleeve, the housing having a first end corresponding to the first end of the sleeve and a second end corresponding to the second end of the sleeve and having a communication port positioned substantially at the first end of the housing, the electronics module communication port engagable with the sleeve communication port
        the housing of the electronic module further comprising a handle at a second end, the handle engagable by a user when the housing is disposed in the sleeve; and
        the electronics module further comprising an information transfer unit, the information transfer unit in communication with relative humidity information from the moisture vapor sensor via the sensor plate communication port and the housing communication port.

2. The moisture vapor probe of claim 1, further comprising a fin positioned circumferentially about the sleeve.

3. The moisture vapor probe of claim 1, wherein the electronics module has a diameter equal to or less than a diameter of the sleeve.

4. The moisture vapor probe of claim 1, further comprising a sensor plate fin extending substantially perpendicular from the sensor plate outer surface.

5. The moisture vapor probe of claim 4, wherein the sensor plate and sensor plate fin define a testing volume of approximately 508 mm$^3$.

6. The moisture vapor probe of claim 1, wherein the information transfer unit comprises one or more of a graphical display, a wireless communication device, a wired communication device, a memory unit and an audio unit.

7. The moisture vapor probe of claim 6, wherein the memory unit is removable from the information transfer unit when positioned in the sleeve.

8. The probe of claim 1, wherein the electronics module is completely disposed within the sleeve.

9. A moisture vapor probe comprising:
- a generally cylindrical hollow sleeve having a sidewall with an inner surface and an outer surface, the sleeve further having a first end and a second end;
the first end having a sensor plate disposed proximate thereto and forming a water impermeable barrier with the sidewall, the second end of the sleeve having an opening such that a volume is defined by the opening, the sidewall and the sensor plate;
  - the sensor plate having an inner surface and an outer surface, a moisture vapor sensor disposed on the outer surface of the sensor plate in electrical communication with a communication port on the inner surface of the sensor plate;
  - an electronics module disposable substantially within the sleeve, the electronics module having a housing shaped to substantially fit within the sleeve, the housing having a first end corresponding to the first end of the sleeve and a second end corresponding to the second end of the sleeve and having a communication port positioned substantially at the first end of the housing, the electronics module communication port engagable with the sleeve communication port;
  - a fin positioned on an exterior of the probe; and
  - the electronics module further comprising an information transfer unit, the information transfer unit in communication with relative humidity information from the moisture vapor sensor via the sensor plate communication port and the housing communication port.

10. The moisture vapor probe of claim 9, wherein the housing of the electronic module further comprises a handle at a second end, the handle engagable by a user when the housing is disposed in the sleeve.

11. The moisture vapor probe of claim 9, wherein the fin is positioned circumferentially about the sleeve.

12. The moisture vapor probe of claim 9, wherein the electronics module has a diameter equal to or less than a diameter of the sleeve.

13. The moisture vapor probe of claim 9, wherein the fin is a sensor plate fin extending substantially perpendicular from the sensor plate outer surface.

14. The moisture vapor probe of claim 13, wherein the sensor plate and sensor plate fin define a testing volume of approximately 508 mm$^3$.

15. The probe of claim 9, wherein the information transfer unit comprises one or more of a graphical display, a wireless communication device, a wired communication device, a memory unit and an audio unit.

16. The moisture vapor probe of claim 15, wherein the memory unit is removable from the information transfer unit when positioned in the sleeve.

17. The moisture vapor probe of claim 9, wherein the electronics module is completely disposed within the sleeve.

\* \* \* \* \*